(12) United States Patent
Seifert et al.

(10) Patent No.: US 12,311,162 B2
(45) Date of Patent: May 27, 2025

(54) HEADER/CONNECTOR THERMAL SPREADER

(71) Applicant: Boston Scientific Scimed, Inc., Maple Grove, MN (US)

(72) Inventors: Kevin R. Seifert, Forest Lake, MN (US); Lisa A. Meyer, Faribault, MN (US); Ramesh Raghupathy, Corcoran, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 785 days.

(21) Appl. No.: 17/378,051

(22) Filed: Jul. 16, 2021

(65) Prior Publication Data
US 2023/0013106 A1    Jan. 19, 2023

(51) Int. Cl.
| | |
|---|---|
| *A61M 60/878* | (2021.01) |
| *A61M 60/178* | (2021.01) |
| *A61M 60/216* | (2021.01) |
| *A61M 60/508* | (2021.01) |
| *A61M 60/873* | (2021.01) |
| *H01R 13/46* | (2006.01) |

(52) U.S. Cl.
CPC ........ *A61M 60/878* (2021.01); *A61M 60/178* (2021.01); *A61M 60/216* (2021.01); *A61M 60/508* (2021.01); *A61M 60/873* (2021.01); *H01R 13/46* (2013.01); *H01R 2201/12* (2013.01)

(58) Field of Classification Search
CPC .......................... A61M 60/878; A61M 60/508
See application file for complete search history.

(56) References Cited

U.S. PATENT DOCUMENTS

| | | |
|---|---|---|
| 6,321,126 B1 | 11/2001 | Kuzma |
| 6,895,276 B2 | 5/2005 | Kast et al. |
| 7,997,854 B2 | 8/2011 | LaRose et al. |
| 8,419,609 B2 | 4/2013 | Shambaugh, Jr. et al. |
| 9,526,522 B2 | 12/2016 | Wood et al. |
| 9,533,082 B2 | 1/2017 | Reichenbach et al. |
| 9,561,053 B2 | 2/2017 | Bonde et al. |
| 9,814,815 B2 | 11/2017 | McSweeney et al. |
| 9,943,294 B2 | 4/2018 | Behymer et al. |
| 9,943,356 B2 | 4/2018 | Bloom et al. |
| 10,286,132 B2 | 5/2019 | McSweeney et al. |

(Continued)

FOREIGN PATENT DOCUMENTS

| | | | |
|---|---|---|---|
| JP | 2015527138 A | * | 9/2015 |
| WO | 2012128777 A1 | | 9/2012 |

*Primary Examiner* — Tammie K Marlen
*Assistant Examiner* — Maria Catherine Anthony
(74) *Attorney, Agent, or Firm* — Seager Tufte & Wickhem, LLP

(57) ABSTRACT

A header for a controller for an implantable medical device. The header includes at least one bore sized and configured to receive a corresponding connector for the implantable medical device. At least one elongate thermally conducting element is disposed within the header and proximate the at least one bore, the at least one elongate thermally conducting element being configured to conduct heat away from the at least one bore and spread heat within the header when the corresponding connector is received within the at least one bore and is communication with the implantable medical device.

20 Claims, 5 Drawing Sheets

(56) References Cited

U.S. PATENT DOCUMENTS

| | | |
|---|---|---|
| 10,300,286 B2 | 5/2019 | Ward et al. |
| 10,541,500 B2 | 1/2020 | Skubitz et al. |
| 2014/0243944 A1* | 8/2014 | Stevenson ............ A61N 1/3752 607/116 |
| 2017/0105762 A1 | 4/2017 | Bloom et al. |
| 2018/0036125 A1 | 2/2018 | Deshmukh et al. |
| 2018/0193008 A1 | 7/2018 | Behymer et al. |
| 2020/0203881 A1* | 6/2020 | Marzano ............. H01R 13/426 |

* cited by examiner

HEADER/CONNECTOR THERMAL SPREADER

CROSS-REFERENCE TO RELATED APPLICATION n/a.

FIELD

The present technology is generally related to implantable controller headers, and in particular, a thermally conductive and heat spreading element disposed within the header.

BACKGROUND

Implantable blood pumps powered by transcutaneous energy transfer systems (TETS) require a significant amount of energy to charge an internal battery of a controller of the pump and to run the pump. This energy results in localized heating where higher resistance components are located within the system. These higher resistance areas are typically located in and insulated by materials with lower heat transfer efficient materials, such as, polyurethane, silicone etc. This combination can result in higher localized heating at interfaces or material deformation and/or degradation.

SUMMARY

The techniques of this disclosure generally relate to implantable controller headers, and in particular, a thermally conductive and heat spreading element disposed within the header.

In one aspect, the present disclosure provides a header for a controller for an implantable medical device. The header includes at least one bore sized and configured to receive a corresponding connector for the implantable medical device. At least one elongate thermally conducting element is disposed within the header and proximate the at least one bore, the at least one elongate thermally conducting element being configured to conduct heat away from the at least one bore and spread heat within the header when the corresponding connector is received within the at least one bore and is communication with the implantable medical device.

In another aspect of this embodiment, the at least one elongate thermally conducting element is a tube disposed adjacent to the at least one bore.

In another aspect of this embodiment, the tube is solid and is composed of a copper core and is cladded with tantalum.

In another aspect of this embodiment, the at least one elongate thermally conducting element is wedge shaped.

In another aspect of this embodiment, the at least one elongate thermally conducting element includes two thermally conducting tubes.

In another aspect of this embodiment, the header further includes a set screw block, and wherein the at least one elongate thermally conducting element is at least partially disposed within the set screw block.

In another aspect of this embodiment, the at least one bore includes two bores, and wherein the at least one elongate thermally conducting element is disposed between the two bores.

In another aspect of this embodiment, the at least one thermally conducting element includes two thermally conducting tubes.

In another aspect of this embodiment, the at least one thermally conducting element includes copper.

In another aspect of this embodiment, the copper is cladded with tantalum.

In one aspect, a header for a controller for an implantable blood pump includes a set screw block disposed within the header. A plurality of bores extends through the set screw block and through at least a portion of the header, the plurality of bores being configured to receive corresponding connectors for the implantable blood pump. At least one elongate thermally conducting element extends through the set screw block and into at least a portion of the header, the at least one elongate thermally conducting element being configured to conduct heat away from the plurality of bores and spread heat within the header when the corresponding connectors are received within the respective one of the plurality of bores and are in communication with the implantable blood pump.

In another aspect of this embodiment, the at least one elongate thermally conducting element is a tube disposed adjacent to the plurality of bores.

In another aspect of this embodiment, the tube is solid and is composed of a copper core and is cladded with tantalum.

In another aspect of this embodiment, the at least one elongate thermally conducting element is wedge shaped.

In another aspect of this embodiment, the at least one thermally conducting element includes two thermally conducting tubes.

In another aspect of this embodiment, the at least one elongate thermally conducting element is disposed between the plurality of bores.

In another aspect of this embodiment, the at least one thermally conducting element includes two thermally conducting tubes.

In another aspect of this embodiment, the two thermally conducting tubes are separated from each other.

In another aspect of this embodiment, the two thermally conducting tubes are axially aligned.

In one aspect, a header for a controller for an implantable blood pump includes a set screw block disposed within the header. A plurality of bores extends through the set screw block and through at least a portion of the header, the plurality of bores being configured to receive corresponding connectors for the implantable blood pump. A plurality of elongate thermally conducting elements extends through the set screw block and into at least a portion of the header, each of the plurality of elongate thermally conducting elements include a solid core tube composed of copper cladded with tantalum and being axially aligned and spaced a distance from each other between the plurality of bores, the plurality of elongate thermally conducting elements being configured to conduct heat away from the plurality of bores and spread heat within the header when the corresponding connectors are received within the respective one of the plurality of bores and are in communication with the implantable blood pump.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

Figure 1:
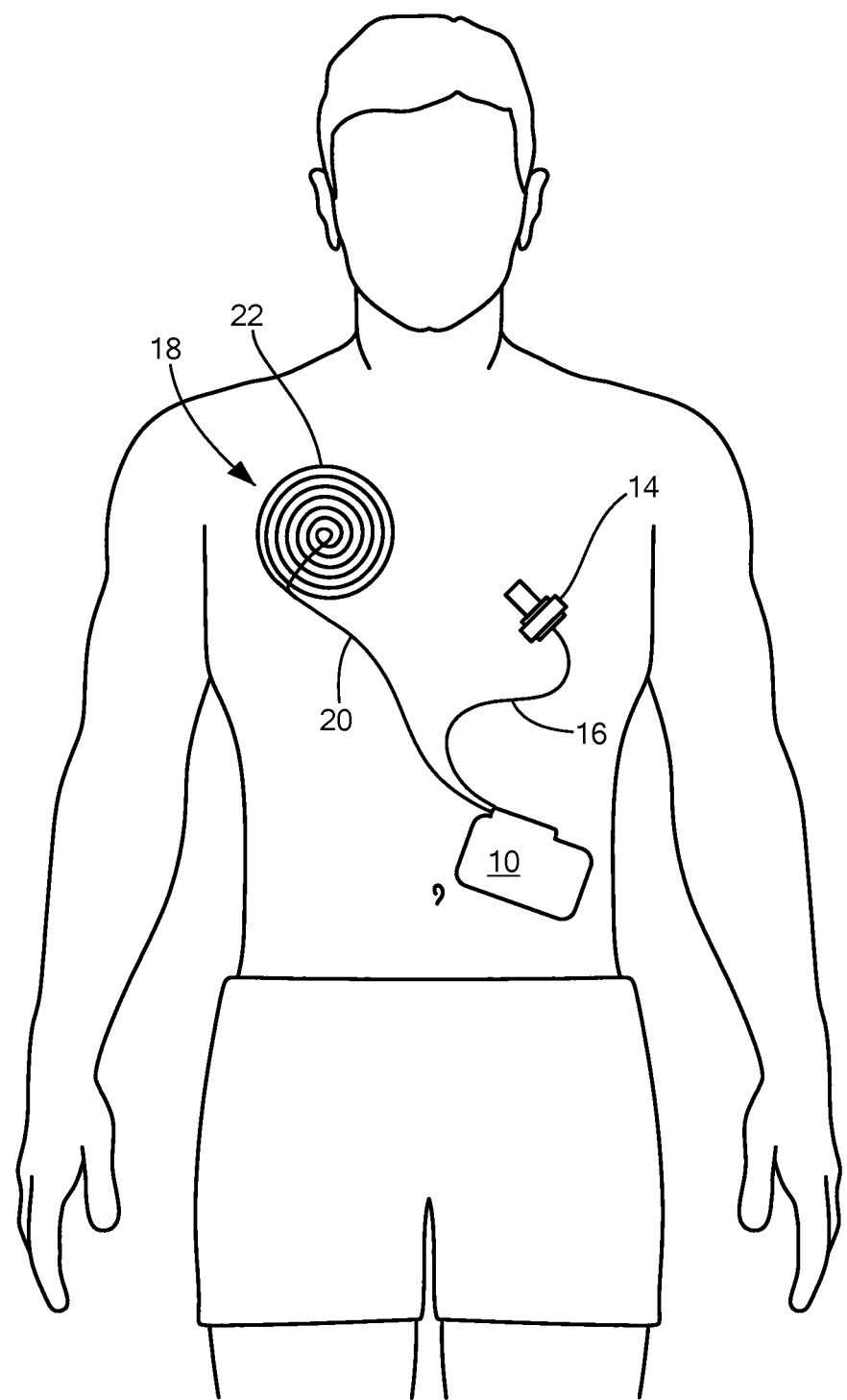
FIG. 1 is a front view of internal components of an implantable blood pump and transcutaneous energy transfer system constructed in accordance with the principles of the present application.

Referring to the drawings in which like reference designators refer to like elements, there is shown in FIG. 1 an exemplary implantable controller for an implantable medical device constructed in accordance with the principles of the present application and designated generally as "10." The controller 10 may include one or more batteries 12 configured to power the components of the controller and provide power one or more implantable medical device, for example, a blood pump such as ventricular assist device (VAD) 14 implanted within the left ventricle of the patient's heart. VADs 14 may include centrifugal pumps, axial pumps, or other kinds electromagnetic pumps configured to pump blood from the heart to blood vessels to circulate around the body. One such centrifugal pump is the HVAD sold by HeartWare, Inc. and is shown and described in U.S. Pat. No. 7,997,854 the entirety of which is incorporated by reference. One such axial pump is the MVAD sold by HeartWare, Inc. and is shown and described in U.S. Pat. No. 8,419,609 the entirety of which is incorporated herein by reference. In an exemplary configuration, the VAD 14 is electrically coupled to the controller 10 by one or more implanted conductors that form a driveline 16 configured to provide power to the VAD 14, relay one or more measured feedback signals from the VAD 14, and/or provide operating instructions to the VAD 14. The controller 10 may include processing circuitry having one or more processors configured to operate the VAD 14 and to processes various signals received from the VAD 14.

Continuing to refer to FIG. 1, a receiving coil 18 may also be coupled to the controller 10 by, for example, one or more implanted conductors 20. In an exemplary configuration, the receiving coil 18 may be implanted subcutaneously proximate the thoracic cavity, although any subcutaneous position may be utilized for implanting the receiving coil 18. The receiving coil 18 is configured to be inductively powered through the patient's skin by a transmission coil (not shown) coupled to an external battery and controller (not shown) disposed opposite the receiving coil 18 on the outside of the patient's body. The receiving coil 18 may be disposed within a hermetically sealed package that does not interfere with the conductivity of the receiving coil 18.

Figure 2:
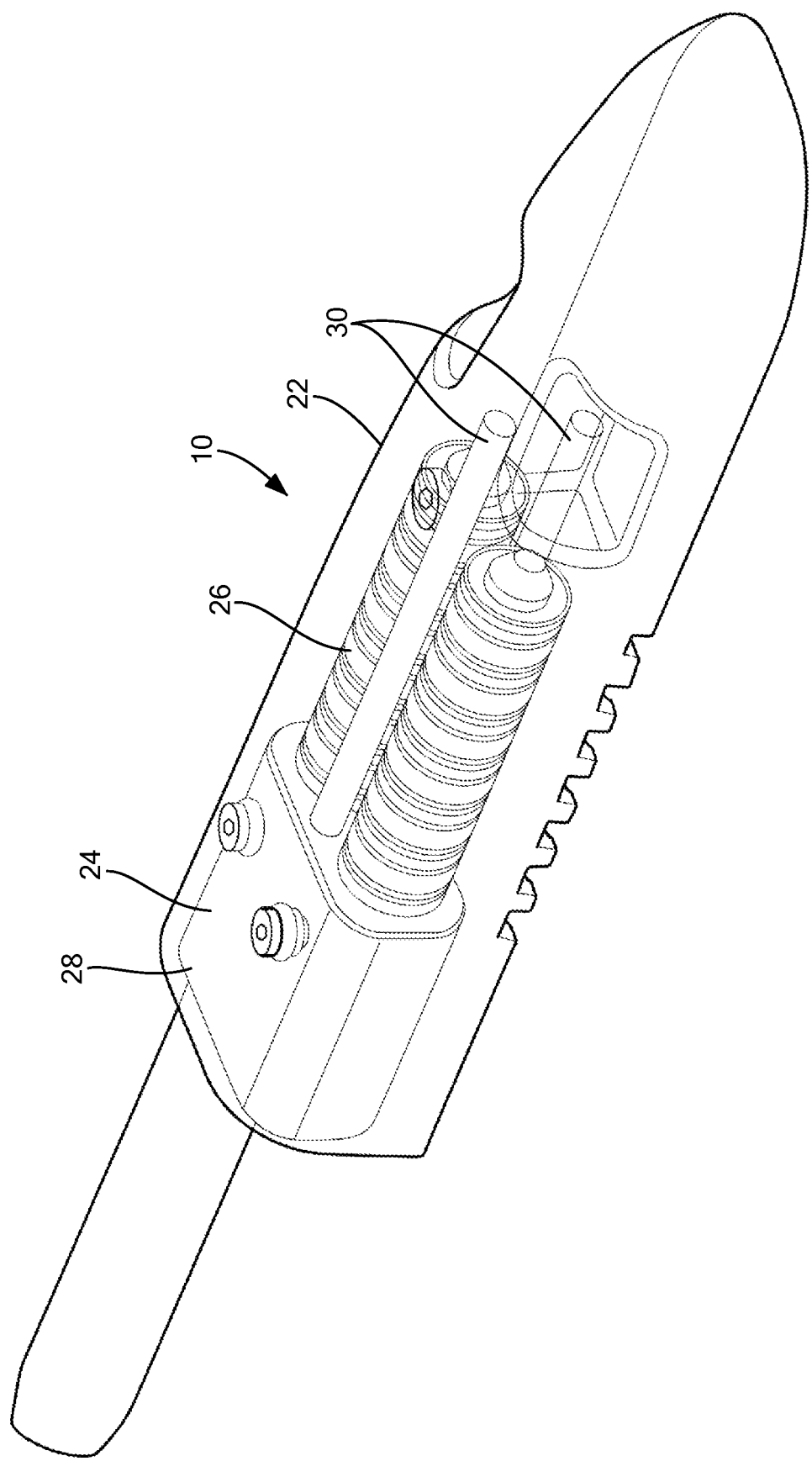
FIG. 2 is a front perspective internal view of a header of the controller shown in FIG. 1.
Figure 3:
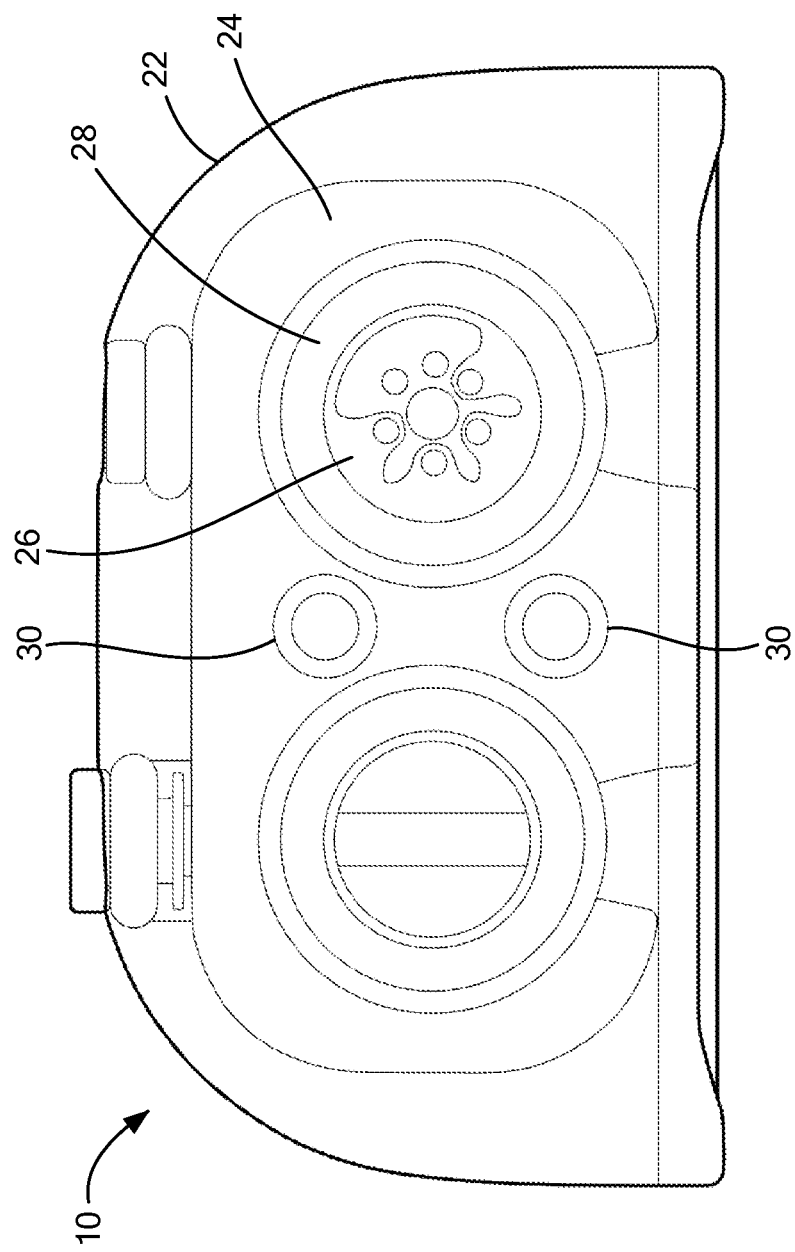
FIG. 3 is a cross-sectional view of the header shown in FIG. 2.

Referring now to FIGS. 2-3 in which a header 22 for the controller 10 is shown. The header 22 includes a set screw block 24 sized and configured to receive one or more connectors 26 which are coupled to the one or more implanted conductors 20 and the driveline 16. The connectors 26 extend through the set screw block 24 and into at least a portion of the header 22 to electrically connect with a plurality of electrical contacts (not shown) to engage the controller 10 with the pump 14 and with the receiving coil 18. In particular, the set screw block 24 defines at least one bore 28 which extends through the set screw block 24 and through the header 22, the at least one bore 28 being sized and configured to receive a corresponding connector 26. At least one thermally conducting element 30 is disposed within the header 22 and proximate the at least one bore 28. For example, the at least one thermally conducting element 30 may be elongated rod, tube, or other shapes and sizes, and configured to conduct heat away from the at least one bore 28 when the corresponding connector is received within the at least one bore 28 and is communication with the implantable medical device 14. In one configuration, the at least one thermally conducting element 30 is a metallic tube, for example, copper, cladded with tantalum, although any biocompatible insulator may be used. For example, the thermally conducting element may have a metallic core such as silver, aluminum, or copper and be cladded with stainless steel, niobium, platinum, or tantalum. In the configuration, shown in FIGS. 1 and 2, the at least one thermally conducting element 30 includes a pair of tantalum clad copper wires extending through the header 22 and the set screw block 24 and disposed between the connector bores 28. In one configuration, the pair of tantalum clad wires are vertically aligned and are disposed side-by-side between the connector bores 28. Although shown as a solid wire, it is contemplated that side-by-side thermally conducting elements 30 may be tubes composed of copper and cladded with tantalum. In the configuration shown in FIG. 2, the thermally conducting elements 30 extend beyond the distal ends of the bores 28, but in other configurations the distal ends of the thermally conducting elements 30 may be proximal to the distal ends of the bores 28 or coterminous. Optionally, although shown as vertically aligned between the bores 28, the thermally conducting elements 30 may be offset from one another or horizontally aligned between the bores.

Figure 4:
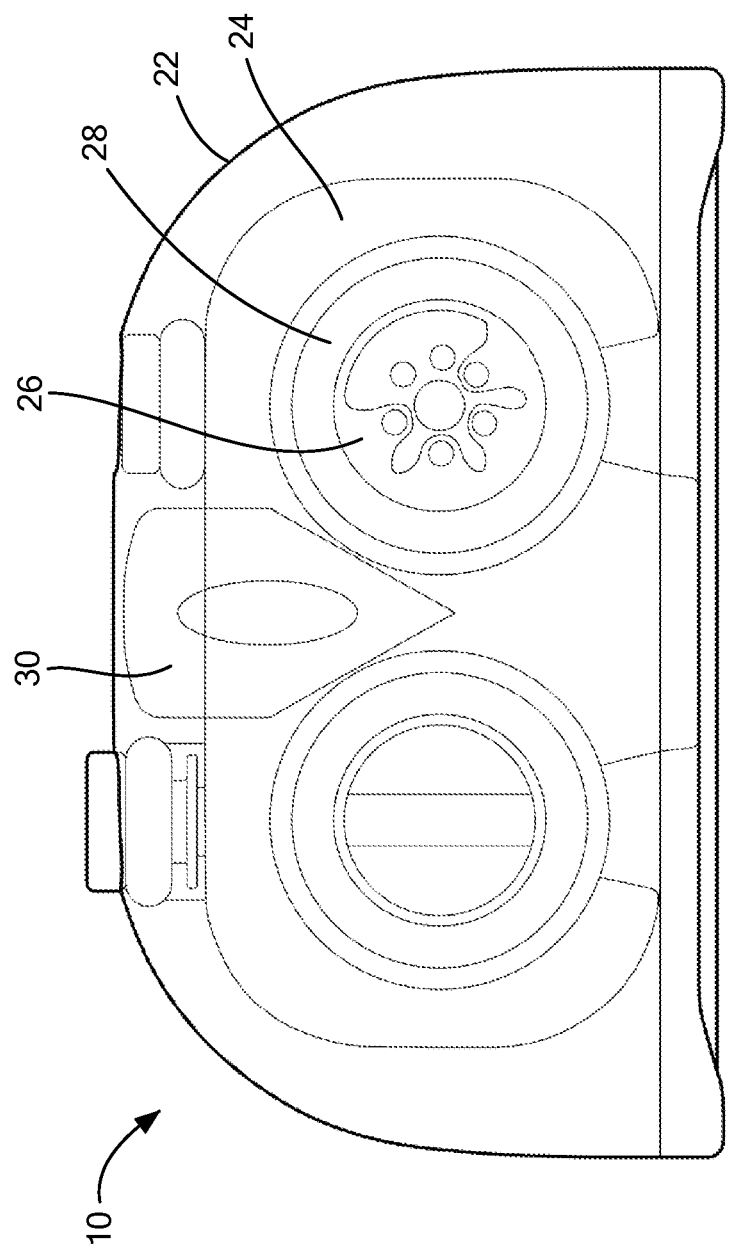
FIG. 4 is a cross-sectional view of another embodiment of the header shown in FIG. 2.
Figure 5:
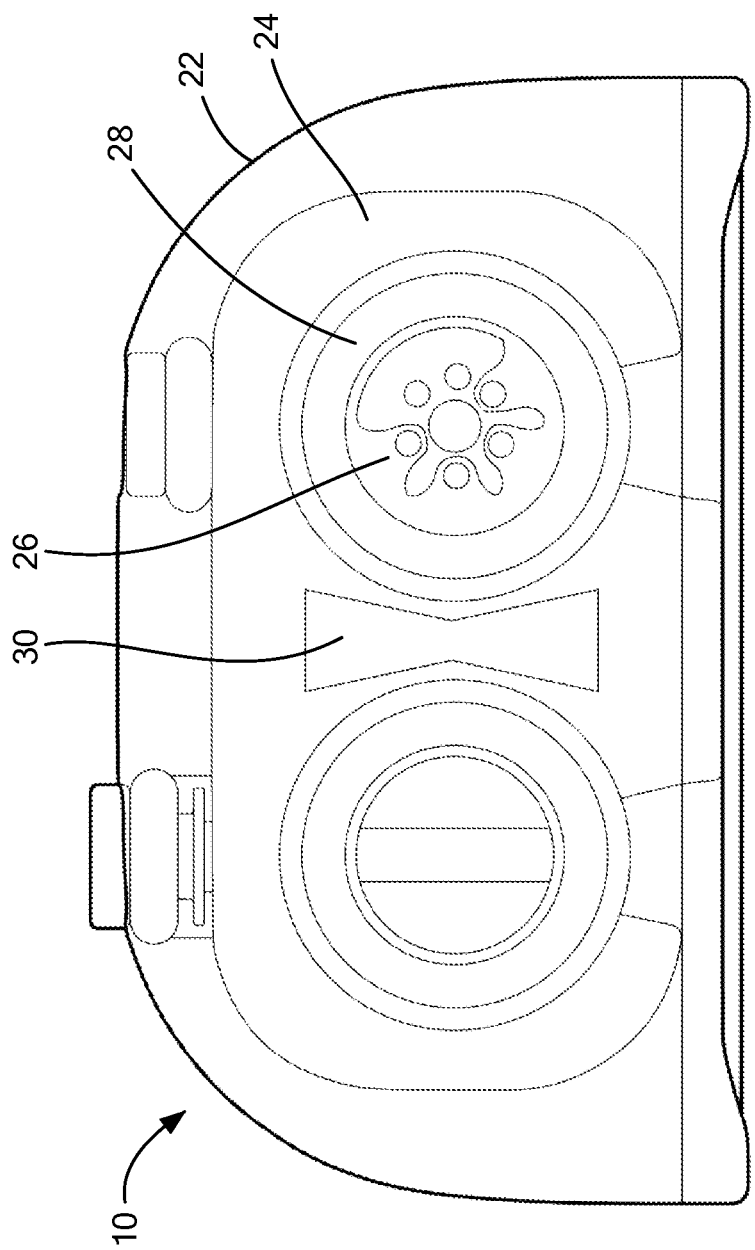
FIG. 5 is a cross-sectional view of another embodiment of the header shown in FIG. 2.

Referring now to FIGS. 4 and 5, the shape and location of the thermally conducting elements 30 may be optimized to spread heat away from electrical contacts within the header 22 and away from the connectors 26 when received within the bores 28. For example, the thermally conducting elements 30 may be shaped to conform to a shape of the bores 28 or to contour, in part, the bores 28. As shown in FIG. 4, the thermally conducting element 30 may define a bow-tie shape such that it conforms, in part, to the contours of the bores 28 surrounding the connectors 26. In the configuration shown in FIG. 4, the thermally conducting element 30 is disposed within the header 22 and the set screw block 24 but not the polyurethane surrounding the set screw block 24. In other configurations, the thermally conducting element 30 may define an oval shaped thermal conductor portion surrounded by a wedge-shaped insulator, as shown in FIG. 5. In the configuration shown in FIG. 5, the wedge-shaped insulator extends into the polyurethane surrounding the set screw block 24 to spread heat toward the surface of the header 22.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A header for a controller for an implantable medical device, the header comprising:
    a body defining at least one bore sized and configured to receive a corresponding connector for the implantable medical device; and
    at least one elongate thermally conducting element disposed within the header and proximate to and outside of the at least one bore, the at least one elongate thermally conducting element being shaped to conform to a shape of the at least one bore and being configured to conduct heat away from the at least one bore and spread heat within the header when the corresponding connector is received within the at least one bore and is in communication with the implantable medical device.

2. The header of claim 1, wherein the at least one elongate thermally conducting element includes a tube disposed adjacent to the at least one bore.

3. The header of claim 2, wherein the tube is solid and includes a copper core and is cladded with tantalum.

4. The header of claim 1, wherein the at least one elongate thermally conducting element is wedge shaped.

5. The header of claim 1, wherein the at least one elongate thermally conducting element includes two thermally conducting tubes.

6. The header of claim 1, further including a set screw block, and wherein the at least one elongate thermally conducting element is at least partially disposed within the set screw block.

7. The header of claim 1, wherein the at least one bore includes two bores, and wherein the at least one elongate thermally conducting element is disposed between the two bores.

8. The header of claim 7, wherein the at least one thermally conducting element includes two thermally conducting tubes.

9. The header of claim 8, wherein the at least one thermally conducting element includes copper.

10. The header of claim 9, wherein the copper is cladded with tantalum.

11. A header for a controller for an implantable blood pump, the header comprising:
    a set screw block defining a plurality of bores, the plurality of bores being configured to receive corresponding connectors for the implantable blood pump; and
    at least one elongate thermally conducting element extending through the set screw block, the at least one elongate thermally conducting element being disposed outside of the plurality of bores and shaped to conform to a shape of the plurality of bores and being configured to conduct heat away from the plurality of bores and spread heat within the header when at least one connector of the corresponding connectors is received within a respective bore of the plurality of bores and is in communication with the implantable blood pump.

12. The header of claim 11, wherein the at least one elongate thermally conducting element includes a tube disposed adjacent to the plurality of bores.

13. The header of claim 12, wherein the tube is solid includes a copper core and is cladded with tantalum.

14. The header of claim 11, wherein the at least one elongate thermally conducting element is wedge shaped.

15. The header of claim 11, wherein the at least one thermally conducting element includes two thermally conducting tubes.

16. The header of claim 11, wherein the at least one elongate thermally conducting element is disposed between the plurality of bores.

17. The header of claim 16, wherein the at least one thermally conducting element includes two thermally conducting tubes.

18. The header of claim 17, wherein the two thermally conducting tubes are separated from each other.

19. The header of claim 17, wherein the two thermally conducting tubes are axially aligned.

20. A header for a controller for an implantable blood pump, the header comprising:
    a set screw block er defining a plurality of bores, the plurality of bores being configured to receive corresponding connectors for the implantable blood pump; and
    a plurality of elongate thermally conducting elements extending through the set screw block, wherein each elongate thermally conducting element of the plurality of elongate thermally conducting elements includes a solid core tube including copper cladded with tantalum, the solid core tube being axially aligned and spaced a distance from each other between and outside of the plurality of bores, the plurality of elongate thermally conducting elements being shaped to conform to a shape of the plurality of bores, the plurality of elongate thermally conducting elements being configured to conduct heat away from the plurality of bores and spread heat within the header when the corresponding connectors are received within the plurality of bores and are in communication with the implantable blood pump.

* * * * *